(12) United States Patent
Vargas et al.

(10) Patent No.: US 9,174,297 B2
(45) Date of Patent: Nov. 3, 2015

(54) RESISTANCE WELDING A POROUS METAL LAYER TO A METAL SUBSTRATE

(75) Inventors: Joseph R. Vargas, Garnerville, NY (US); Steven Seelman, Montclair, NJ (US); Clarence M. Panchison, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 188 days.

(21) Appl. No.: 13/300,151

(22) Filed: Nov. 18, 2011

(65) Prior Publication Data
US 2012/0125896 A1    May 24, 2012

Related U.S. Application Data

(60) Provisional application No. 61/414,978, filed on Nov. 18, 2010.

(51) Int. Cl.
| | | |
|---|---|---|
| *B23K 9/00* | (2006.01) | |
| *B23K 11/18* | (2006.01) | |
| *A61F 2/30* | (2006.01) | |
| *A61F 2/36* | (2006.01) | |
| *B23K 11/16* | (2006.01) | |

(52) U.S. Cl.
CPC ............... *B23K 11/18* (2013.01); *A61F 2/3094* (2013.01); *A61F 2/30907* (2013.01); *A61F 2/36* (2013.01); *B23K 11/163* (2013.01); *A61F 2002/3092* (2013.01); *A61F 2002/30451* (2013.01); *A61F 2002/30981* (2013.01); *A61F 2310/00023* (2013.01); *A61F 2310/00407* (2013.01)

(58) Field of Classification Search
CPC .............................. B23K 11/18; B23K 11/163
USPC ................................................... 219/108, 118
See application file for complete search history.

(56) References Cited

U.S. PATENT DOCUMENTS

| | | | |
|---|---|---|---|
| 3,905,777 A | | 9/1975 | LaCroix |
| 4,636,219 A | * | 1/1987 | Pratt et al. .................... 623/23.3 |
| 4,660,755 A | | 4/1987 | Farling et al. |

(Continued)

FOREIGN PATENT DOCUMENTS

| | | |
|---|---|---|
| CN | 103221000 A | 7/2013 |
| FR | 2215927 A1 | 8/1974 |

OTHER PUBLICATIONS

International Search Report and Written Opinion mailed Mar. 20, 2012 in the related International Patent Application No. PCT/US2011/061454.

(Continued)

*Primary Examiner* — Dana Ross
*Assistant Examiner* — Ayub Maye
(74) *Attorney, Agent, or Firm* — Schwegman Lundberg & Woessner, P.A.

(57) ABSTRACT

An apparatus and method are provided for manufacturing an orthopedic prosthesis by resistance welding a porous metal layer of the orthopedic prosthesis onto an underlying metal substrate of the orthopedic prosthesis. The resistance welding process involves directing an electrical current through the porous layer and the substrate, which dissipates as heat to cause softening and/or melting of the materials, especially along the interface between the porous layer and the substrate. The softened and/or melted materials undergo metallurgical bonding at points of contact between the porous layer and the substrate to fixedly secure the porous layer onto the substrate.

21 Claims, 11 Drawing Sheets

(56) References Cited

U.S. PATENT DOCUMENTS

| | | | |
|---|---|---|---|
| 4,829,152 A | 5/1989 | Rostoker et al. | |
| 4,863,474 A | 9/1989 | Brown et al. | |
| 5,443,510 A | 8/1995 | Shetty et al. | |
| 5,734,959 A | 3/1998 | Krebs et al. | |
| 6,214,049 B1 * | 4/2001 | Gayer et al. | 623/16.11 |
| 6,222,150 B1 * | 4/2001 | Nomura et al. | 219/78.02 |
| 6,485,533 B1 * | 11/2002 | Ishizaki et al. | 51/307 |
| 2011/0073581 A1 * | 3/2011 | Ma | 219/137.31 |
| 2013/0180970 A1 | 7/2013 | Vargas et al. | |
| 2014/0151342 A1 | 6/2014 | Vargas et al. | |

OTHER PUBLICATIONS

Partial Search Report mailed Feb. 2, 2012 in related International Application No. PCT/US2011/061454.

"International Application Serial No. PCT/US2011/061454, International Preliminary Report on Patentability mailed May 30, 2013", 10 pgs.

U.S. Appl. No. 14/175,036, filed Feb. 7, 2014, Resistance Welding a Porous Metal Layer to a Metal Substrate.

U.S. Appl. No. 13/787,150, filed Mar. 6, 2013, Resistance Welding a Porous Metal Layer to a Metal Substrate.

"U.S. Appl. No. 14/175,036, Preliminary Amendment filed Feb. 19, 2014", 7 pgs.

"Chinese Application Serial No. 201180055421.9, Amendment filed Nov. 11, 2013", (W/English Translation), 6 pgs.

"Chinese Application Serial No. 201180055421.9, Voluntary Amendment filed Feb. 24, 2014", (W/English Translation of Claims), 7 pgs.

"European Application Serial No. 11791389.7, Office Action mailed Jul. 30, 2013", 2 pgs.

"European Application Serial No. 11791389.7, Response filed Feb. 10, 2014", 4 pgs.

* cited by examiner

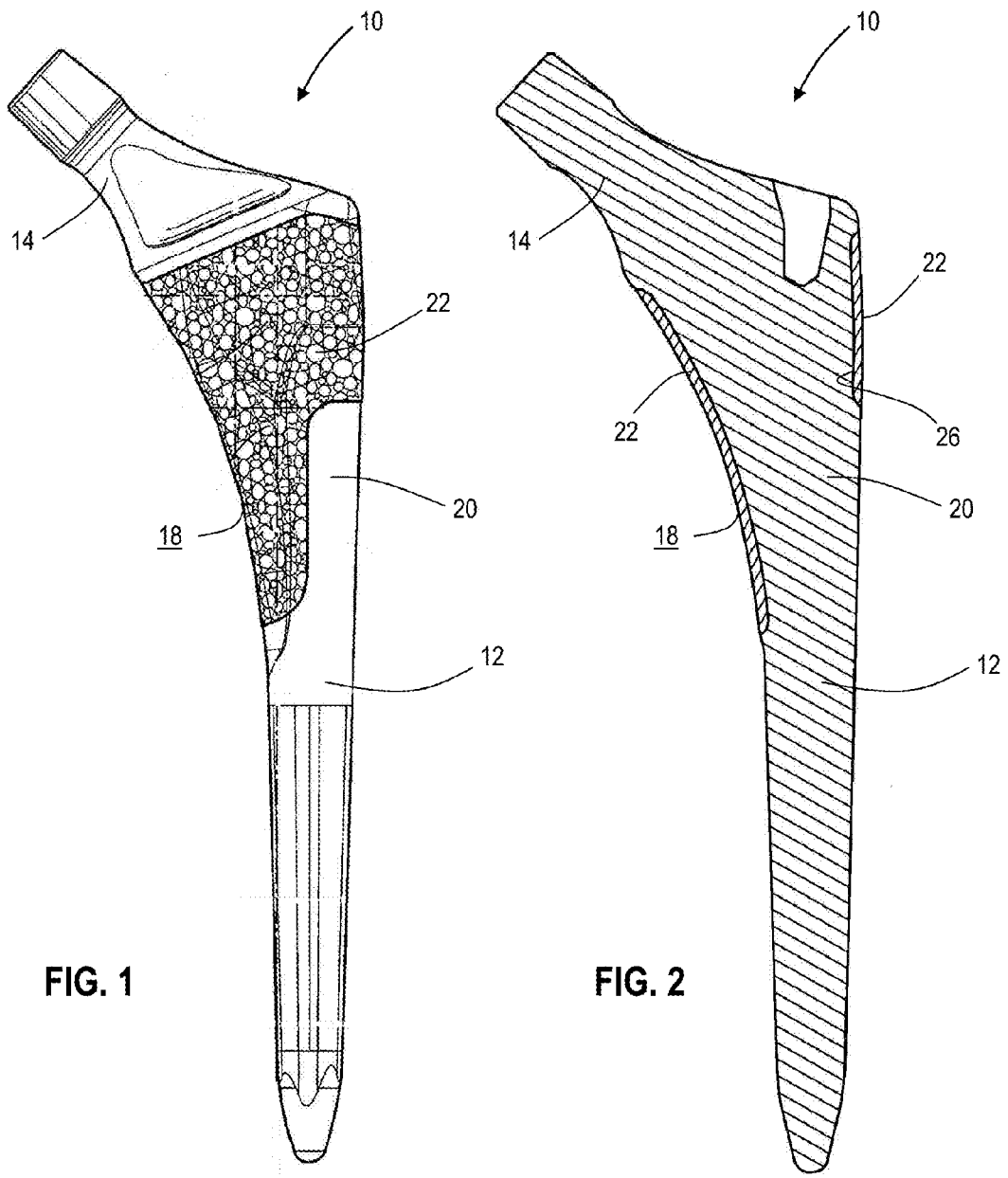

RESISTANCE WELDING A POROUS METAL LAYER TO A METAL SUBSTRATE

CROSS REFERENCE TO RELATED APPLICATION

This application claims priority from U.S. Provisional Patent Application Ser. No. 61/414,978, filed Nov. 18, 2010, the disclosure of which is hereby expressly incorporated by reference herein in its entirety.

FIELD OF THE DISCLOSURE

The present disclosure relates to a method of manufacturing an orthopedic prosthesis. More particularly, the present disclosure relates to a method of manufacturing an orthopedic prosthesis having a porous metal layer and an underlying metal substrate.

BACKGROUND OF THE DISCLOSURE

Orthopedic prostheses are commonly used to replace at least a portion of a patient's joint to restore or increase the use of the joint following traumatic injury or deterioration due to aging, illness, or disease, for example.

To enhance the fixation between an orthopedic prosthesis and a patient's bone, the orthopedic prosthesis may be provided with a porous metal layer. The porous metal layer may define at least a portion of the bone-contacting surface of the prosthesis to encourage bone growth and/or soft tissue growth into the prostheses. The porous metal layer may be coupled to an underlying metal substrate.

SUMMARY

The present disclosure provides an apparatus and method for manufacturing an orthopedic prosthesis by resistance welding a porous metal layer of the orthopedic prosthesis onto an underlying metal substrate of the orthopedic prosthesis. The resistance welding process involves directing an electrical current through the porous layer and the substrate, which dissipates as localized heat to cause softening and/or melting of the materials, especially at points of contact along the interface between the porous layer and the substrate. The softened and/or melted materials undergo metallurgical bonding at the points of contact between the porous layer and the substrate to fixedly secure the porous layer onto the substrate.

According to an embodiment of the present disclosure, a method is provided for manufacturing an orthopedic prosthesis. The method includes the steps of: providing a metal substrate; providing a porous metal layer having a thickness; positioning the porous layer against the substrate to form an interface between the porous layer and the substrate; and directing an electrical current to the interface between the porous layer and the substrate to bond the porous layer to the substrate while maintaining the thickness of the porous layer.

According to another embodiment of the present disclosure, a method is provided for manufacturing an orthopedic prosthesis having a metal substrate and a porous metal layer. The method includes the steps of: positioning the porous layer against the substrate to form an interface between the porous layer and the substrate; and directing a pulsed electrical current to the interface between the porous layer and the substrate to bond the porous layer to the substrate, the pulsed electrical current including at least a first pulse and a second pulse separated from the first pulse by a cooling time.

According to yet another embodiment of the present disclosure, a method is provided for manufacturing an orthopedic prosthesis. The method includes the steps of: providing a metal substrate; providing a porous metal layer having a net surface; positioning the net surface of the porous layer against the substrate to form an interface between the porous layer and the substrate; and directing an electrical current to the interface between the porous layer and the substrate to bond the porous layer to the substrate. The net surface of the porous layer is formed by: providing a porous structure having an outer surface; coating the outer surface of the porous structure with metal to produce the porous layer; and after the coating step, maintaining the outer surface without machining the outer surface to arrive at the net surface.

According to still yet another embodiment of the present disclosure, an apparatus is provided for manufacturing an orthopedic prosthesis having a metal substrate and a porous metal layer. The apparatus includes a housing defining a chamber with a controlled atmosphere, the chamber sized to receive the orthopedic prosthesis, a controller, a power source, and an electrode configured to establish electrical communication between the power source and the orthopedic prosthesis, the controller directing a pulsed electrical current from the power source to the orthopedic prosthesis to bond the porous layer to the substrate.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein:

FIG. 1 is an elevational view of a prosthetic proximal femoral component, the proximal femoral component including a porous metal layer coupled to an underlying metal substrate;

FIG. 2 is a cross-sectional view of the proximal femoral component of FIG. 1;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 3:
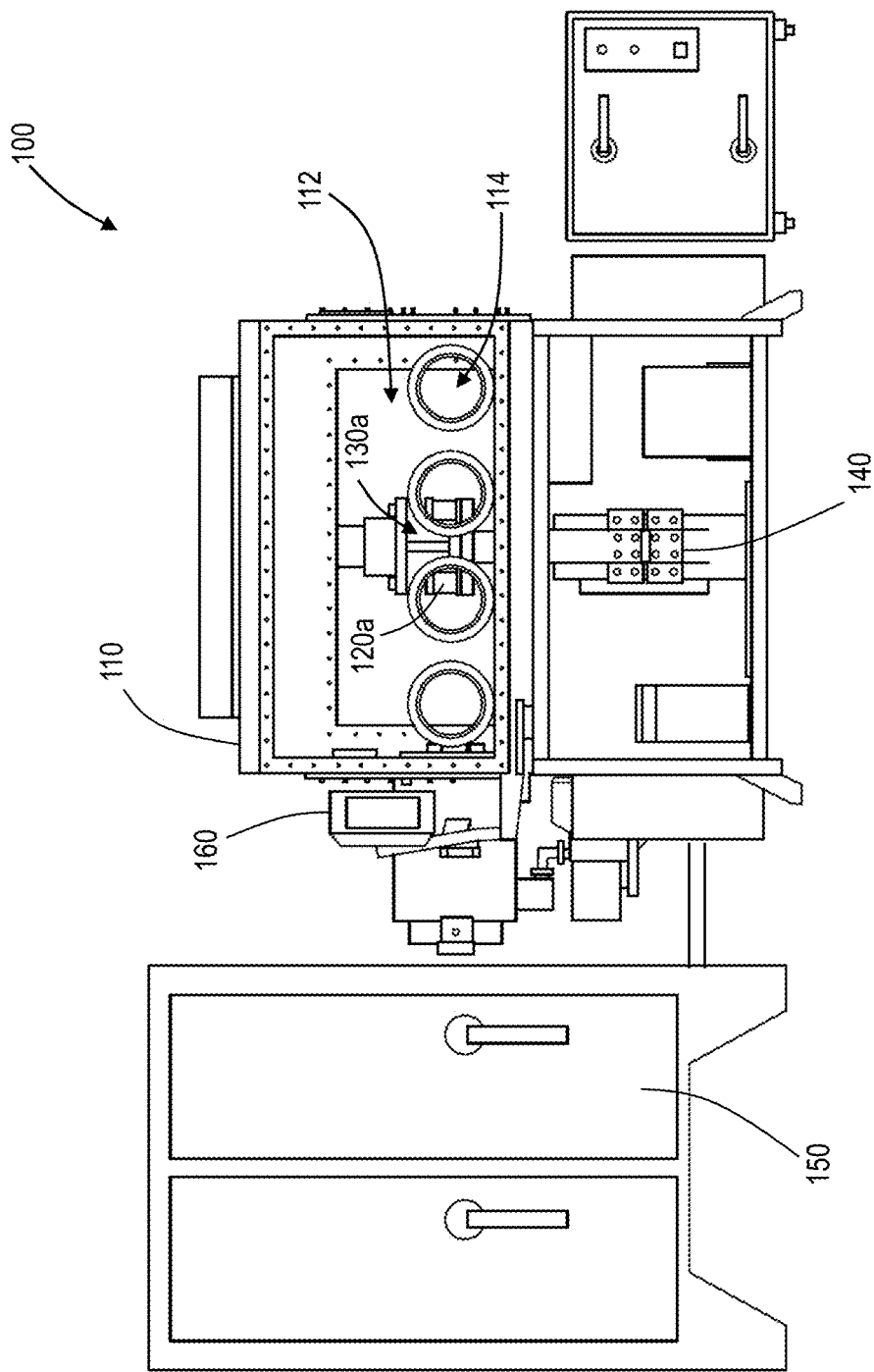
FIG. 3 is a front elevational view of an exemplary apparatus used to assemble the proximal femoral component of FIG. 1.

Referring to FIGS. 1 and 2, an orthopedic prosthesis is provided in the form of a proximal femoral component 10 (e.g., a hip stem). While the orthopedic prosthesis is described and depicted herein in the form of a proximal femoral component 10, the orthopedic prosthesis may also be in the form of a distal femoral component, a tibial component, an acetabular component, or a humeral component, for example.

Proximal femoral component 10 of FIG. 1 includes stem 12 and neck 14, which is configured to receive a modular head (not shown). It is also within the scope of the present disclosure that the head may be integrally coupled to neck 14. In use, with stem 12 of proximal femoral component 10 implanted into the intramedullary canal of a patient's proximal femur, neck 14 and the head (not shown) of proximal femoral component 10 extend medially from the patient's proximal femur to articulate with the patient's natural acetabulum or a prosthetic acetabular component. Stem 12 of proximal femoral component 10 includes an exterior, bone-contacting surface 18 that is configured to contact bone and/or soft tissue of the patient's femur.

As shown in FIG. 2, proximal femoral component 10 includes a metal substrate 20 and a porous metal layer 22 coupled to the underlying substrate 20. Porous layer 22 may be disposed within recess 26 of substrate 20. With porous layer 22 defining at least a portion of bone-contacting surface 18, bone and/or soft tissue of the patient's femur may grow into porous layer 22 over time to enhance the fixation (i.e., osseointegration) between proximal femoral component 10 and the patient's femur.

Substrate 20 of proximal femoral component 10 may comprise a biocompatible metal, such as titanium, a titanium alloy, cobalt chromium, cobalt chromium molybdenum, tantalum, or a tantalum alloy. According to an exemplary embodiment of the present disclosure, substrate 20 comprises a Ti-6Al-4V ELI alloy, such as Tivanium® which is available from Zimmer, Inc., of Warsaw, Ind. Tivanium® is a registered trademark of Zimmer, Inc.

Porous layer 22 of proximal femoral component 10 may comprise a biocompatible metal, such as titanium, a titanium alloy, cobalt chromium, cobalt chromium molybdenum, tantalum, or a tantalum alloy. Porous layer 22 may be in the form of a highly porous biomaterial, which is useful as a bone substitute and as cell and tissue receptive material. It is also within the scope of the present disclosure that porous layer 22 may be in the form of a fiber metal pad or a sintered metal layer, such as a Cancellous-Structured Titanium™ (CSTi™) layer, for example. CSTi™ porous layers are manufactured by Zimmer, Inc., of Warsaw, Ind. Cancellous-Structured Titanium™ and CSTi™ are trademarks of Zimmer, Inc.

A highly porous biomaterial may have a porosity as low as 55%, 65%, or 75% and as high as 80%, 85%, or 90%, or within any range defined between any pair of the foregoing values. An example of such a material is a highly porous fiber metal pad. Another example of such a material is a CSTi™ layer. Yet another example of such a material is produced using Trabecular Metal™ technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of proximal femoral component 10 to the patient's femur.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an optimized matrix for bone ingrowth and mineralization.

When porous layer 22 of proximal femoral component 10 is produced using Trabecular Metal™ technology, as discussed above, a small percentage of substrate 20 may be in direct contact with the ligaments of porous layer 22. For example, approximately 15%, 20%, or 25%, of the surface area of substrate 20 may be in direct contact with the ligaments of porous layer 22.

Referring next to FIG. 3, apparatus 100 is provided for resistance welding porous layer 22 to substrate 20 of proximal femoral component 10. Apparatus 100 is also illustrated schematically in FIGS. 4A and 4B. Apparatus 100 includes housing 110, one or more braces or fixtures 120a, 120b, one or more weld heads 130a, 130b, within housing 110, each having an electrode 132a, 132b, transformer 140, a power source or current generator 150, and controller 160. Each component of apparatus 100 is described further below.

Housing 110 of apparatus 100 defines an internal chamber 112 that is sized to receive at least one prosthesis, such as proximal femoral component 10 of FIGS. 1 and 2. According to an exemplary embodiment of the present disclosure, housing 110 of apparatus 100 creates a vacuum environment or an inert environment in chamber 112 during the resistance welding process. In one particular example, chamber 112 of housing 110 is flushed with an inert gas (e.g., argon) and controlled to have a dew point less than about −60° C. and an oxygen concentration less than about 10 ppm.

Housing 110 may be at least partially transparent to enable a user to see inside chamber 112. Also, housing 110 may include one or more openings 114 to enable a user to access chamber 112. To maintain a vacuum environment or an inert environment in chamber 112, housing 110 may be in the form of a glovebox. In other words, each opening 114 may include a glove (not shown) or another suitable barrier that extends into chamber 112 to receive the user's hand while maintaining a seal around opening 114.

Fixtures 120a, 120b, of apparatus 100 contact proximal femoral component 10 to hold proximal femoral component 10 in place within housing 110 of apparatus 100. Fixtures 120a, 120b, may be moved apart to an open position (FIG. 4A) to receive proximal femoral component 10, and then fixtures 120a, 120b, may be moved together to a closed or clamped position (FIG. 4B) to hold proximal femoral component 10 in place. It is within the scope of the present disclosure that the closed position of fixtures 120a, 120b, may be adjustable to enable apparatus 100 to receive and hold prostheses of different shapes and sizes.

Figure 4A:
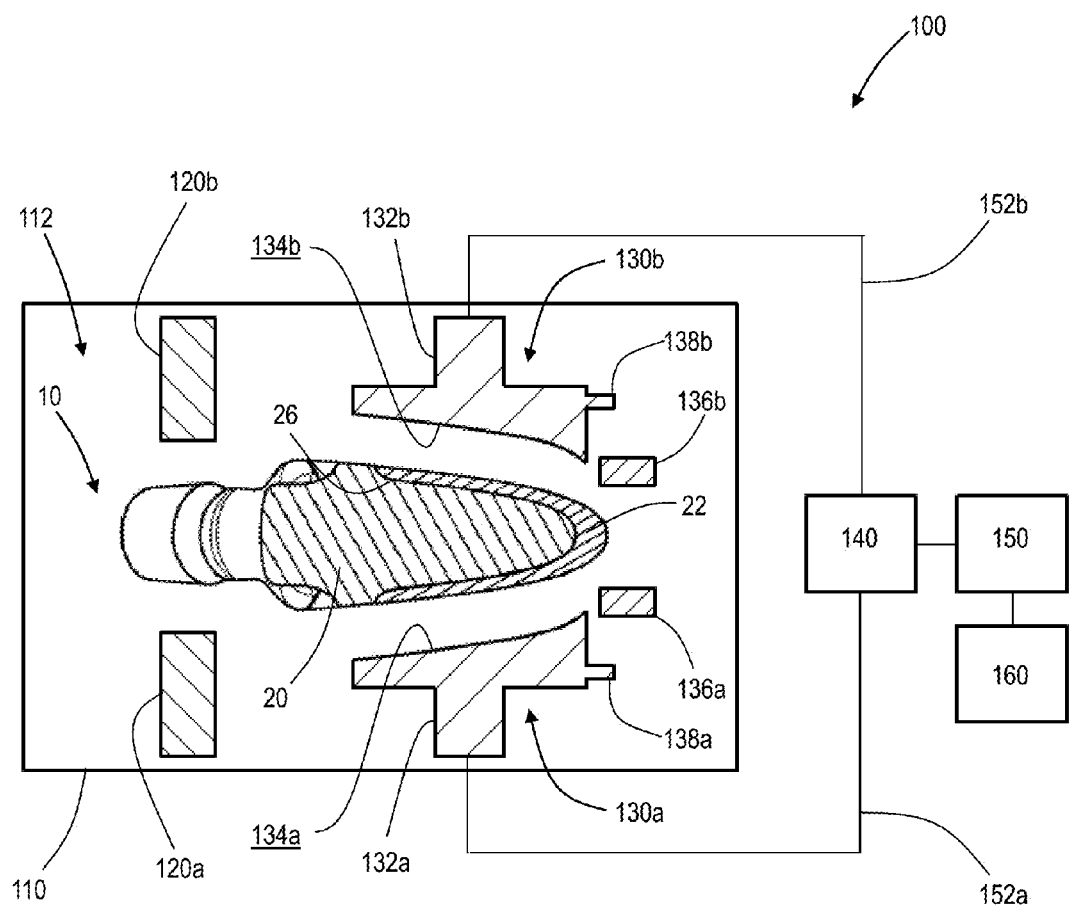
FIG. 4A is a schematic diagram of the apparatus of FIG. 3, the apparatus including fixtures and weld heads that are shown in an open position to receive the proximal femoral component.

Electrodes 132a, 132b, on weld heads 130a, 130b, of apparatus 100 are connected to transformer 140 and current generator 150 via wires 152a, 152b, respectively. As shown in FIG. 4A, each electrode 132a, 132b, faces a corresponding side of porous layer 22. More specifically, contact surface 134a, 134b, of each electrode 132a, 132b, faces a corresponding side of porous layer 22. According to an exemplary embodiment of the present disclosure, contact surface 134a, 134b, of each electrode 132a, 132b, is designed to substantially match the contour of the corresponding side of porous layer 22. In this embodiment, each electrode 132a, 132b, is able to make close, even contact with proximal femoral component 10. Depending on the shape of proximal femoral component 10, the corresponding contact surface 134a, 134b, may be concave, convex, or planar, for example.

Weld heads 130a, 130b, of apparatus 100 may be configured to hold porous layer 22 against substrate 20 during the resistance welding process. More particularly, weld heads 130a, 130b, may be configured to hold porous layer 22 within recess 26 of substrate 20 during the resistance welding process. Like fixtures 120a, 120b, described above, weld heads 130a, 130b, may be moved away from proximal femoral component 10 to an open position (FIG. 4A) to receive proximal femoral component 10, and then weld heads 130a, 130b, may be moved toward proximal femoral component 10 to a closed or clamped position (FIG. 4B) to hold porous layer 22 within recess 26 of substrate 20. The open and/or closed positions of weld heads 130a, 130b, may be controlled using one or more stops 136a, 136b, that contact corresponding flanges 138a, 138b, on weld heads 130a, 130b, to limit movement of electrodes 132a, 132b. It is within the scope of the present disclosure that the closed position of each weld head 130a, 130b, may be adjustable, such as by moving stops 136a, 136b, to enable apparatus 100 to receive and hold prostheses of different shapes and sizes.

Optionally, apparatus 100 may include additional braces or fixtures (not shown) that are configured to hold porous layer 22 against substrate 20 during the resistance welding process. More particularly, these additional fixtures may be configured to hold porous layer 22 within recess 26 of substrate 20 during the resistance welding process.

The pressure used to hold porous layer 22 against substrate 20 of proximal femoral component 10 during the resistance welding process may be sufficiently low to avoid deforming or compressing porous layer 22 while still resisting movement of porous layer 22 relative to substrate 20. Thus, the weld pressure should not exceed the compressive yield strength of substrate 20 or porous layer 22. If the compressive yield strength of porous layer 22 is about 4,000 psi (27.6 MPa), for example, a suitable weld pressure may be as low as 100 psi (0.7 MPa), 500 psi (3.4 MPa), or 1,000 psi (6.9 MPa), and as high as 2,000 psi (13.8 MPa), 2,500 psi (17.2 MPa), or 3,000 psi (20.7 MPa), or within any range defined between any pair of the foregoing values, for example. Porous layer 22 may be provided in a substantially final shape before the resistance welding process to avoid having to compress or otherwise shape porous layer 22 during the resistance welding process. As a result, the thickness of porous layer 22 and the contact area between porous layer 22 and substrate 20 may remain substantially unchanged during the resistance welding process. As discussed above, the weld pressure may be applied by weld heads 130a, 130b, when weld heads 130a, 130b, are in the closed position (FIG. 4B) and/or by additional fixtures (not shown) of apparatus 100.

Figure 4B:
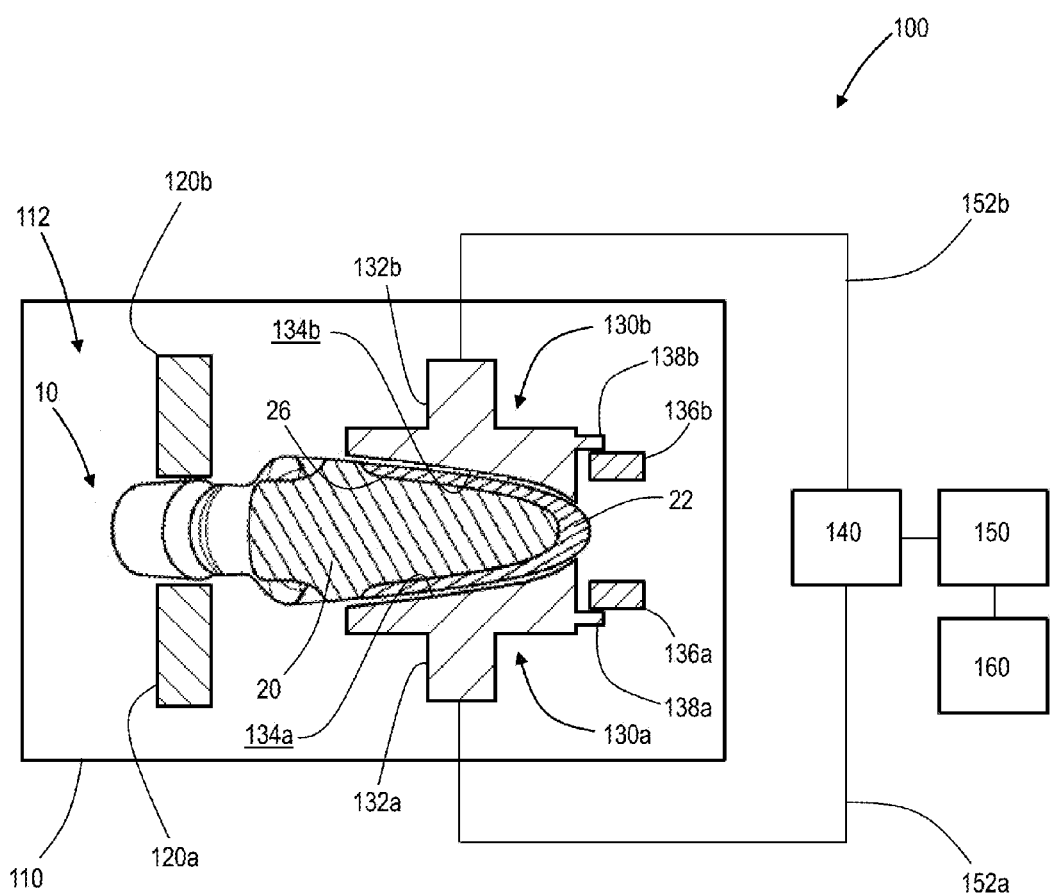
FIG. 4B is a schematic diagram similar to FIG. 4A, the fixtures and the weld heads of the apparatus shown in a closed position to hold the porous metal layer against the metal substrate of the proximal femoral component.

Controller 160 of apparatus 100, which may be in the form of a general purpose computer, is coupled to transformer 140 and current generator 150 to control the operation of electrodes 132a, 132b. Controller 160 of apparatus 100 may also control the evacuation of housing 110 and/or the flushing of housing 110 with an inert gas (e.g., argon). Additionally, controller 160 of apparatus 100 may control movement of fixtures 120a, 120b, and/or weld heads 130a, 130b, between their respective open positions (FIG. 4A) and closed positions (FIG. 4B).

In use, proximal femoral component 10 is loaded into housing 110 of apparatus 100. With porous layer 22 properly disposed against substrate 20 of proximal femoral component 10, controller 160 may be operated to move fixtures 120a, 120b, and/or weld heads 130a, 130b, from their respective open positions (FIG. 4A) toward their respective closed positions (FIG. 4B). The approach pressure (i.e. the pressure at which fixtures 120a, 120b, and/or weld heads 130a, 130b, approach proximal femoral component 10 before making contact with proximal femoral component 10) may be less than the above-described weld pressure to avoid damaging the components. For example, the approach pressure may be as low as 10 psi (0.07 MPa), 30 psi (0.2 MPa), or 50 psi (0.3 MPa), and as high as 70 psi (0.5 MPa), 90 psi (0.6 MPa), or 110 psi (0.8 MPa), or within any range defined between any pair of the foregoing values.

After proximal femoral component 10 is loaded into housing 110 of apparatus 100, controller 160 may be operated to evacuate chamber 112 of housing 110 and/or to flush chamber 112 of housing 110 with an inert gas (e.g., argon). The vacuum or inert environment within housing 110 of apparatus 100 may substantially prevent proximal femoral component 10 from oxidizing, absorbing atmospheric contaminants, and/or becoming discolored during the resistance welding process.

Controller 160 may then continue moving fixtures 120a, 120b, and weld heads 130a, 130b, into their respective closed positions (FIG. 4B) to hold both porous layer 22 and substrate 20 of proximal femoral component 10 in place within housing 110. As discussed above, the weld pressure (i.e., the pressure at which fixtures 120a, 120b, and/or weld heads 130a, 130b, come to hold proximal femoral component 10 during the resistance welding process) may be as low as 100 psi (0.7

MPa), 500 psi (3.4 MPa), or 1,000 psi (6.9 MPa), and as high as 2,000 psi (13.8 MPa), 2,500 psi (17.2 MPa), or 3,000 psi (20.7 MPa), for example.

Next, controller 160 may be operated to initiate current flow from current generator 150 to transformer 140. Current generator 150 may operate at a power of 4 kJ, 6 kJ, 8 kJ, 10 kJ, or more, for example. With contact surface 134a, 134b, of each electrode 132a, 132b, positioned against porous layer 22 of proximal femoral component 10, the weld current flows from one electrode (e.g., electrode 132a via wire 152a), through proximal femoral component 10, and out of the other electrode (e.g., electrode 132b via wire 152b). In an exemplary embodiment, the source electrode 132a, 132b, may deliver a weld current to proximal femoral component 10 as low as 20 kA, 30 kA, or 40 kA, and as high as 50 kA, 60 kA, or 70 kA, or within any range defined between any pair of the foregoing values, for example, to produce weld current densities as low as 25 kA/in$^2$ (3.9 kA/cm$^2$), 35 kA/in$^2$ (5.4 kA/cm$^2$), or 45 kA/in$^2$ (7.0 kA/cm$^2$), and as high as 55 kA/in$^2$ (8.5 kA/cm$^2$), 65 kA/in$^2$ (10.1 kA/cm$^2$), 75 kA/in$^2$ (11.6 kA/cm$^2$), or 85 kA/in$^2$ (13.2 kA/cm$^2$), or within any range defined between any pair of the foregoing values. As the weld current flows through proximal femoral component 10, controller 160 may maintain the weld pressure of fixtures 120a, 120b, and/or weld heads 130a, 130b.

According to Ohm's Law ($P=I^2*R$), the weld current (I) that flows through porous layer 22 and substrate 20 of proximal femoral component 10 dissipates as heat, with the amount of heat generated being proportional to the resistance (R) at any point in the electrical circuit. When different materials are used to construct porous layer 22 and substrate 20, the resistance (R) may be highest at the interface between porous layer 22 and substrate 20. Therefore, a large amount of heat may be generated locally at points of contact between porous layer 22 and substrate 20.

According to an exemplary embodiment of the present disclosure, the heat generated is sufficient to cause softening and/or melting of the materials used to construct porous layer 22 and/or substrate 20 which, in combination with the weld pressure used to hold porous layer 22 against substrate 20, causes surface metallurgical bonding to occur at points of contact between porous layer 22 and substrate 20. It is also within the scope of the present disclosure that metallurgical bonding may occur at points of contact within porous layer 22. For example, if porous layer 22 is in the form of a fiber metal pad, metallurgical bonding may occur at points of contact between adjacent metal wires within the fiber metal pad.

According to another exemplary embodiment of the present disclosure, the weld current may be delivered to proximal femoral component 10 in discrete but rapid pulses. The weld current may be delivered to proximal femoral component 10 with as few as 4, 6, or 8 pulses and as many as 10, 12, or 14 pulses, or any value therebetween, for example. Each pulse may be as short as 20 milliseconds, 40 milliseconds, or 60 milliseconds, and as long as 80 milliseconds, 100 milliseconds, or 120 milliseconds, or any value therebetween, for example. Between each pulse, the absence of a weld current may promote bulk cooling of porous layer 22 and substrate 20 without eliminating localized, interfacial heating of porous layer 22 and substrate 20. The cooling time between each pulse may be less than 1 second, and more specifically may be as short as 20 milliseconds, 40 milliseconds, or 60 milliseconds, and as long as 80 milliseconds, 100 milliseconds, or 120 milliseconds, or any value therebetween, for example.

As discussed above, the weld pressure used to hold porous layer 22 against substrate 20 during the resistance welding process should be sufficiently low to avoid deforming porous layer 22. Due to softening and/or melting of substrate 20 along the interface, porous layer 22 may shift or translate slightly toward the softened substrate 20 and may become embedded within the softened substrate 20. Therefore, the total thickness of proximal femoral component 10 (i.e., the combined thickness of porous layer 22 and substrate 20) may decrease during the resistance welding process. For example, the total thickness of proximal femoral component 10 may decrease by approximately 0.1%, 0.2%, 0.3%, or more, during the resistance welding process. However, the thickness of porous layer 22 itself should not substantially change. In other words, any measurable change in thickness of proximal femoral component 10 should result from porous layer 22 shifting into the softened substrate 20, not from the compaction or deformation of porous layer 22 itself. When porous layer 22 is in the form of a fiber metal pad, porous layer 22 may undergo some deformation (e.g., shrinkage) due to the formation of metallurgical bonds within porous layer 22. However, this deformation should not be attributed to the weld pressure.

After delivering current to proximal femoral component 10, substrate 20 and porous layer 22 will begin to cool. During this time, controller 160 may be operated to maintain a forge pressure on the components. The forge pressure (i.e. the pressure at which fixtures 120a, 120b, and/or weld heads 130a, 130b, hold proximal femoral component 10 after the weld current ceases) may be less than the above-described weld pressure. For example, the forge pressure may be as low as 40 psi (0.3 MPa), 60 psi (0.4 MPa), or 80 psi (0.6 MPa) and as high as 100 psi (0.7 MPa), 120 psi (0.8 MPa), or 140 psi (1.0 MPa), or within any range defined between any pair of the foregoing values. The forge time may be as short as 1 second, 2 seconds, or 3 seconds, and as long as 4 seconds, 5 seconds, or more, for example.

In total, the time required to resistance weld porous layer 22 to substrate 20 using apparatus 100 may be as short as 1 second, 10 seconds, 20 seconds, or 30 seconds, and as long as 1 minute, 2 minutes, 3 minutes, or more, for example. The time required may vary depending on the thickness of porous layer 22, the current generated by current generator 150, and other parameters.

Finally, controller 160 may be operated to return fixtures 120a, 120b, and/or weld heads 130a, 130b, to their respective open positions (FIG. 4A). Proximal femoral component 10 may then be removed from housing 110 of apparatus 100 with porous layer 22 fixedly secured to substrate 20.

Advantageously, by resistance welding porous layer 22 onto substrate 20, a strong metallurgical bond may be achieved between porous layer 22 and substrate 20. In certain embodiments, the bond strength between porous layer 22 and substrate 20 may be at least 2,900 psi (20.0 MPa), which is the FDA-recommended bond strength for orthopedic implants. Also, because resistance welding involves localized, interfacial heating of porous layer 22 and substrate 20 and requires short cycle times, degradation of porous layer 22 and substrate 20 may be avoided. As a result, the fatigue strength of substrate 20 and porous layer 22 may be substantially unchanged during the resistance welding process.

Although porous layer 22 is described and depicted herein as being bonded directly to substrate 20 of proximal femoral component 10, it is also within the scope of the present disclosure that porous layer 22 may be pre-bonded to an intermediate layer (not shown), which is then subsequently bonded to substrate 20. A suitable intermediate layer may include, for example, a titanium foil. Both the pre-bonding step between porous layer 22 and the intermediate layer and the subsequent bonding step between the intermediate layer and substrate 20 may involve resistance welding, as described above with reference to FIGS. 3, 4A, and 4B. However, it is also within the scope of the present disclosure that the subsequent bonding step between the intermediate layer and substrate 20 may involve traditional, diffusion bonding.

EXAMPLES

1. Example #1

Analysis of Trabecular Metal™ Surface Finish and Thickness

A series of samples were prepared, each sample having a disc-shaped porous component produced using Trabecular Metal™ technology and a disc-shaped Tivanium® substrate. The substrates were substantially the same, but the porous components differed in two aspects—surface finish and thickness—as set forth in Table 1 below.

TABLE 1

| Group | | Interfacing Surface Finish of Porous Component | Porous Component Thickness (inches) |
|---|---|---|---|
| 1 | A | Electro discharge machined (EDM) | 0.060 |
|   | B | Electro discharge machined (EDM) | 0.125 |
|   | C | Electro discharge machined (EDM) | 0.250 |
| 2 | A | Net shape | 0.060 |
|   | B | Net shape | 0.125 |
|   | C | Net shape | 0.250 |
| 3 | A | Smeared | 0.060 |
|   | B | Smeared | 0.125 |
|   | C | Smeared | 0.250 |

Before placing the interfacing surface of each porous component against its corresponding substrate, the interfacing surface of each porous component was treated as set forth in Table 1 above.

In Group 1, the interfacing surface of each porous component was subjected to electro discharge machining (EDM), which broke off some protruding ligaments of the porous component and leveled the interfacing surface, making more ligaments available at the interfacing surface to contact the underlying substrate. Therefore, EDM moderately increased the net contact area of the porous components in Group 1.

In Group 2, each porous component was provided in a net shape and the interfacing surface of each porous component was not subjected to machining after manufacturing, so the bulk porosity of the porous component was retained at the interfacing surface. More specifically, the net-shaped interfacing surface was produced by coating an outer surface of a porous structure (e.g., a reticulated vitreous carbon foam structure) with metal and then maintaining the outer, coated surface without machining or shaping the outer surface. Therefore, the net contact area of the porous components in Group 2 was retained.

In Group 3, the interfacing surface of each porous component was subjected to physical machining to break off some ligaments of the porous component and spread out or "smear" other ligaments of the porous component, which caused a substantial reduction in the surface porosity of the interfacing surface. Therefore, smearing increased the net contact area of the porous components in Group 3.

As a result of these surface treatments, the porous components of Group 2 had the least surface contact with the underlying substrate, while the porous components of Group 3 had the most surface contact with the underlying substrate.

The samples were then assembled by resistance welding. A first quantity of power was applied to weld the 0.060 inch (1.5 mm) thick and the 0.125 inch (3.2 mm) thick porous components (Groups 1A, 1B, 2A, 2B, 3A, and 3B) to their corresponding substrates. A second quantity of power 50% greater than the first quantity of power was applied to weld the 0.250 inch (6.4 mm) thick porous components (Groups 1C, 2C, and 3C) to their corresponding substrates. The average bond strength for the samples of each Group 1-3 is depicted graphically in FIG. 5.

Figure 5:
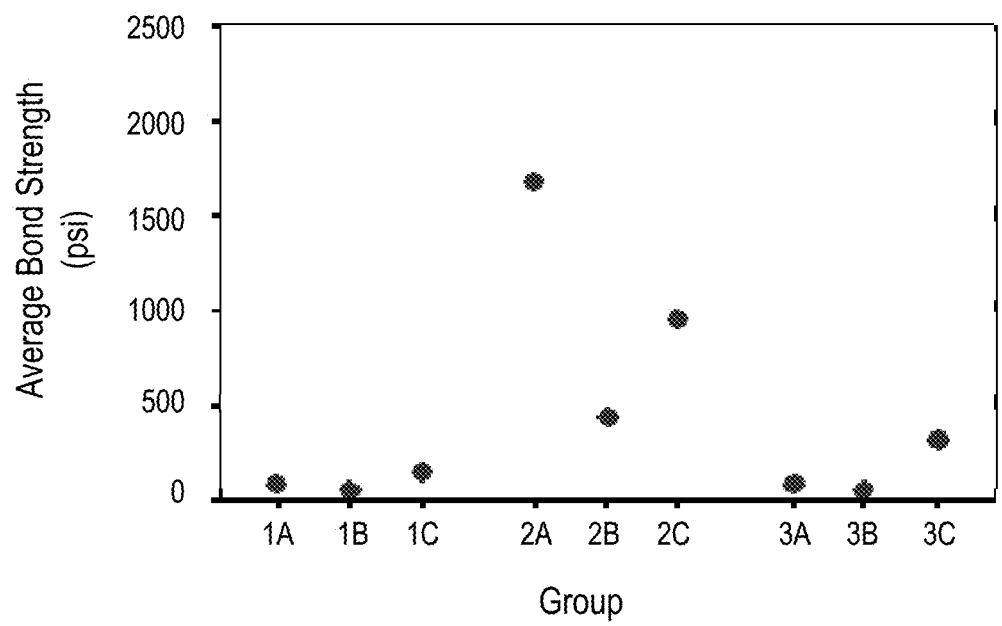
FIG. 5 is a graphical depiction of the average bond strength between various porous layers and metal substrates in accordance with Example #1.

As shown in FIG. 5, the samples of Group 2 had higher average bond strengths than the samples of Groups 1 or 3. Because the porous components of Groups 1 and 3 had more surface contact with the underlying substrates than the samples of Group 2, the inventors suspect that the applied current and heat dissipated across the greater surface contact area, resulting in weaker bonds for the samples of Groups 1 and 3 than the samples of Group 2. In contrast, because the porous components of Group 2 had less surface contact with the underlying substrates than the samples of Groups 1 and 3, the inventors suspect that the applied current and heat was localized at each individual ligament, resulting in stronger bonds for the samples of Group 2 than the samples of Groups 1 and 3.

Also, within each Group 1-3, the samples of subgroups A and C had higher average bond strengths than the samples of the corresponding subgroup B. For example, the samples of Groups 2A and 2C had higher average bond strengths than the samples of Group 2B.

The decrease in bond strength from subgroup A to B within each Group 1-3 may be attributed to the increased thickness of the porous components from 0.060 inch to 0.125 inch. Because the thermal conductivity of tantalum in each porous component (about 54 W/m/K) is greater than the thermal conductivity of titanium in each substrate (about 7 W/m/K), the thicker porous components of each subgroup B may act as heat sinks, conducting the heat generated at the interface away from the interface and into the volume of the porous component.

The increase in bond strength from subgroup B to C within each Group 1-3 may be attributed to the 50% increase between the first quantity of power used to resistance weld the 0.060 inch thick and the 0.125 inch thick porous components and the second quantity of power used to resistance weld the 0.250 inch thick porous components. The increased power produces increased current flow, which results in greater heating and a stronger bond.

2. Example #2

Analysis of Trabecular Metal™ Thickness, Weld Power, and Number of Weld Cycles

Another series of samples were prepared, each sample having a disc-shaped porous component produced using Trabecular Metal™ technology and a disc-shaped Tivanium® substrate. Because the net-shaped porous components (Group 2) achieved the highest bond strengths in Example #1, the porous components of Example #2 were also provided in a net shape. The substrates were substantially the same, but the porous components differed in thickness. Also, the resistance welding process differed in two aspects—power and number of weld cycles—as set forth in Table 2 below.

TABLE 2

| Group | | Porous Component Thickness (inches) | Weld Power (kJ) | Number of Weld Cycles |
|---|---|---|---|---|
| 4 | A | 0.060 | 6 | 1 |
|   | B | 0.060 | 6 | 2 |
| 5 | A | 0.125 | 6 | 1 |
|   | B | 0.125 | 6 | 2 |
| 6 | A | 0.125 | 9 | 1 |
|   | B | 0.125 | 9 | 2 |

Figure 6:
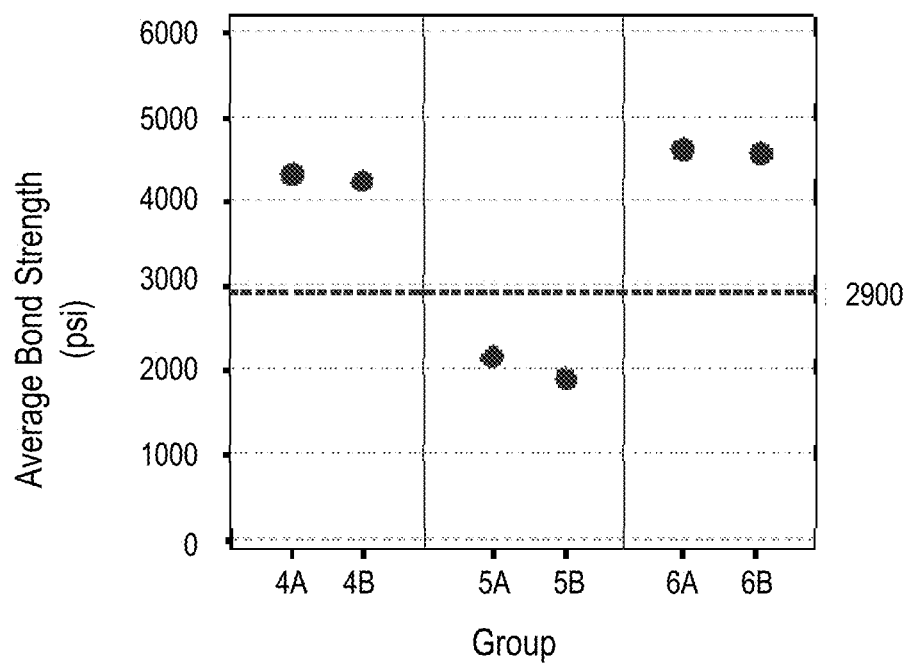
FIG. 6 is another graphical depiction of the average bond strength between various porous layers and metal substrates in accordance with Example #2.

The average bond strength for the samples of each Group 4-6 is depicted graphically in FIG. 6. The samples of Groups 4 and 6 had higher average bond strengths than the samples of Group 5. In fact, the samples of Groups 4 and 6 had average bond strengths above 4,000 psi (27.6 MPa), which exceeds the FDA-recommended bond strength of 2,900 psi (20.0 MPa).

About 90.6% of the variation in bond strength may be attributed to the varied thickness of the porous components and the varied weld power. The number of weld cycles was found to be statistically insignificant.

3. Example #3

Analysis of Trabecular Metal™ Thickness and Weld Time

Another series of circular samples were prepared, each sample having a disc-shaped porous component produced using Trabecular Metal™ technology and a disc-shaped Tivanium® substrate. The contact area between each porous component and its underlying substrate was about 5 square inches (32.3 cm²). The substrates were substantially the same, but the porous components differed in thickness. Also, the resistance welding cycle time differed, as set forth in Table 3 below.

TABLE 3

| Group | | Porous Component Thickness (inches) | Weld Time (milliseconds) |
|---|---|---|---|
| 7 | A | 0.060 | 150 |
|   | B | 0.060 | 200 |
|   | C | 0.060 | 250 |
| 8 | A | 0.125 | 150 |
|   | B | 0.125 | 200 |
|   | C | 0.125 | 250 |

Figure 7:
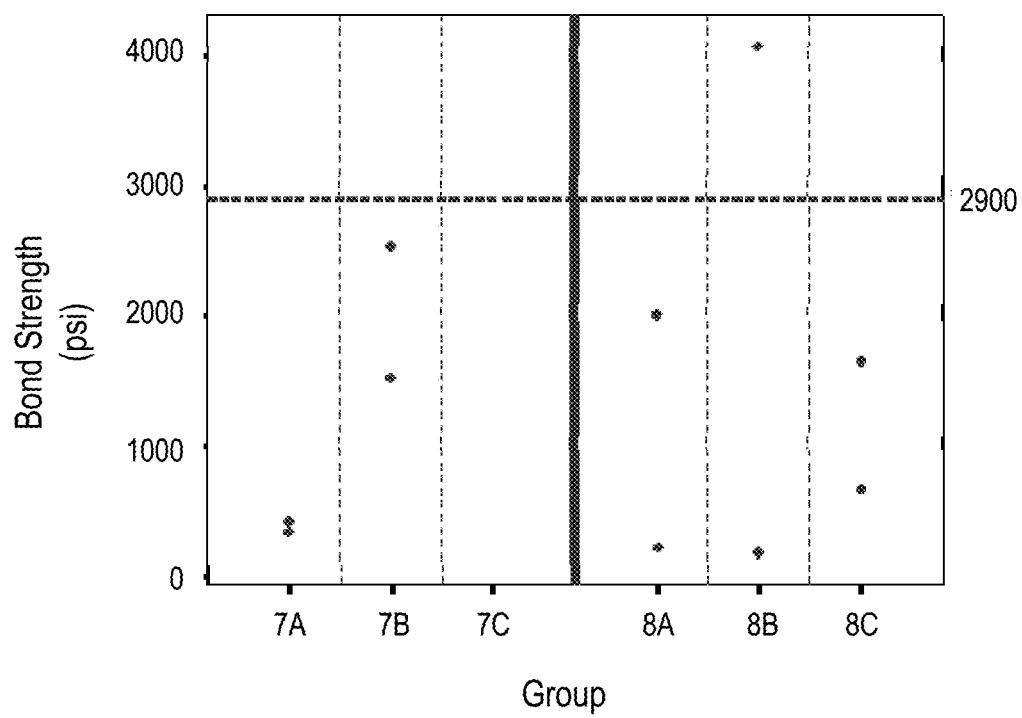
FIG. 7 is another graphical depiction of the bond strength between various porous layers and metal substrates in accordance with Example #3.

After resistance welding the samples, two 1.2 inch (3.0 cm) diameter test coupons were cut from each sample for tensile testing. The bond strength for each test coupon of Groups 7 and 8 is depicted graphically in FIG. 7. As shown in FIG. 7, one of the two test coupons of Group 8B had a bond strength greater than the FDA-recommended bond strength of 2,900 psi (20.0 MPa). However, the other test coupon of Group 8B had a bond strength less than 1,000 psi (6.9 MPa).

The variation in bond strength between corresponding test coupons may be due to non-uniform pressure and/or current across each sample. Physical examination of the remnant material left behind after cutting the 1.2 inch (3.0 cm) diameter test coupons supported the finding of varying levels of bond strength within each sample.

4. Example #4

Comparison between Resistance Welding and Diffusion Bonding

In addition to tensile testing, metallography was also performed to compare the bond achieved with resistance welding to the bond achieved with diffusion bonding.

Figure 8:
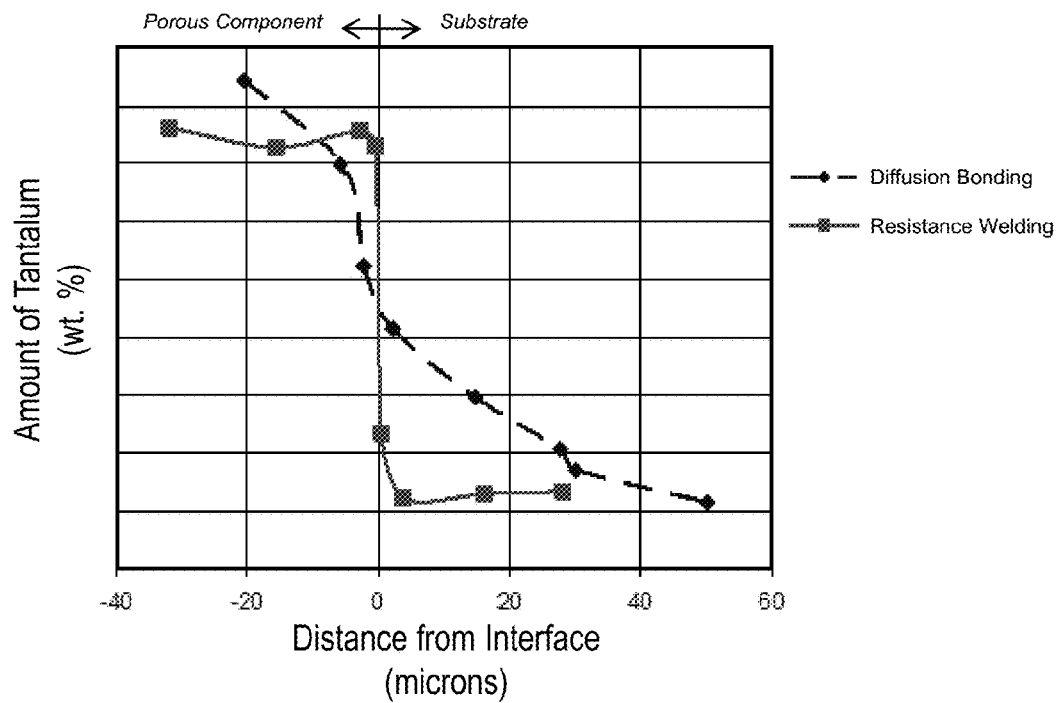
FIG. 8 is a graphical depiction of the tantalum concentration gradient in a diffusion bonded sample and in a resistance welded sample.
Figure 9:
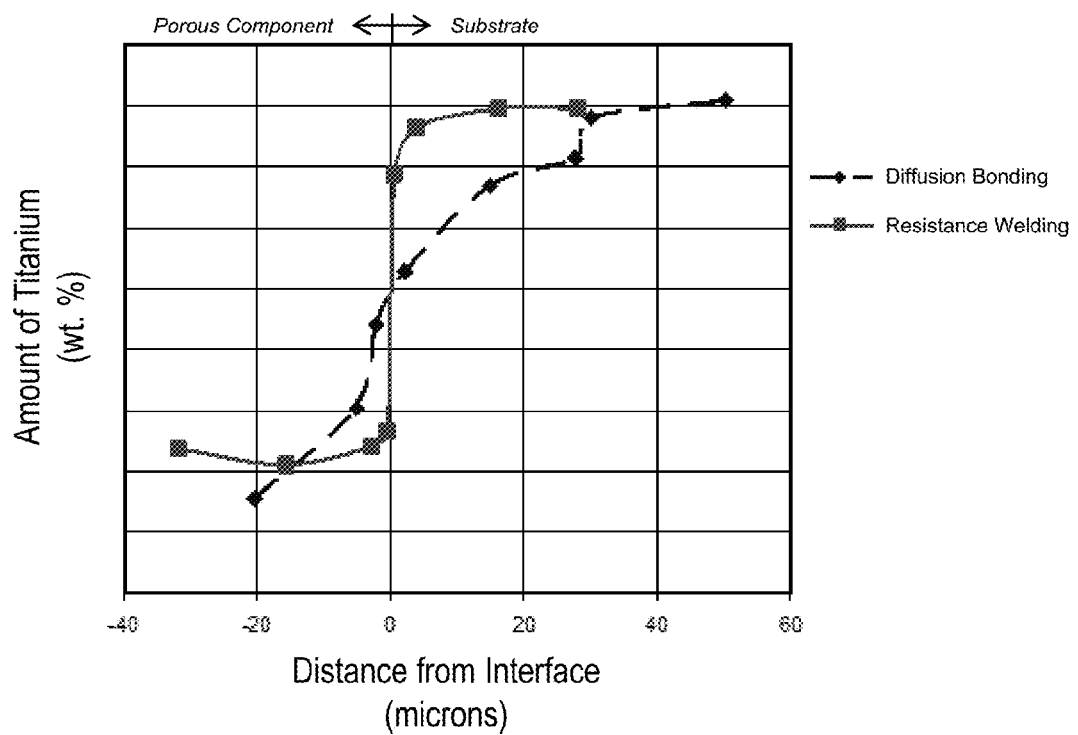
FIG. 9 is a graphical depiction of the titanium concentration gradient in a diffusion bonded sample and in a resistance welded sample.
Figure 10:
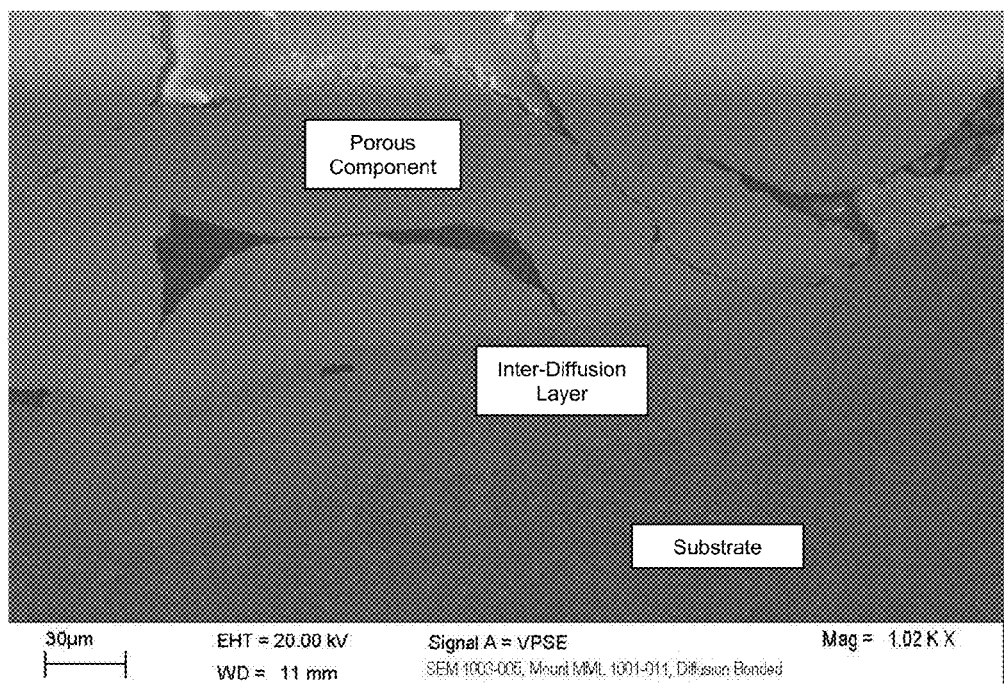
FIG. 10 is a scanning electron microscope image taken along the interface between a porous component and a substrate of a diffusion bonded sample.

When a porous component is diffusion bonded to an underlying substrate, atoms from the porous component and atoms from the substrate inter-diffuse. For example, when a porous component produced using Trabecular Metal™ technology is diffusion bonded to a Tivanium® substrate, tantalum from the porous component diffuses into the substrate, and titanium from the substrate diffuses into the porous component. The diffusion of tantalum into the substrate is shown graphically in FIG. 8, and the diffusion of titanium into the porous component is shown graphically in FIG. 9. The inter-diffusion of tantalum and titanium creates a concentration gradient or an inter-diffusion layer along the interface between the porous component and the substrate. The inter-diffusion layer between the porous component and the substrate is also shown visually in FIG. 10, which is a scanning electron microscope image taken along the interface between the porous component and the substrate of a diffusion bonded sample.

Figure 11:
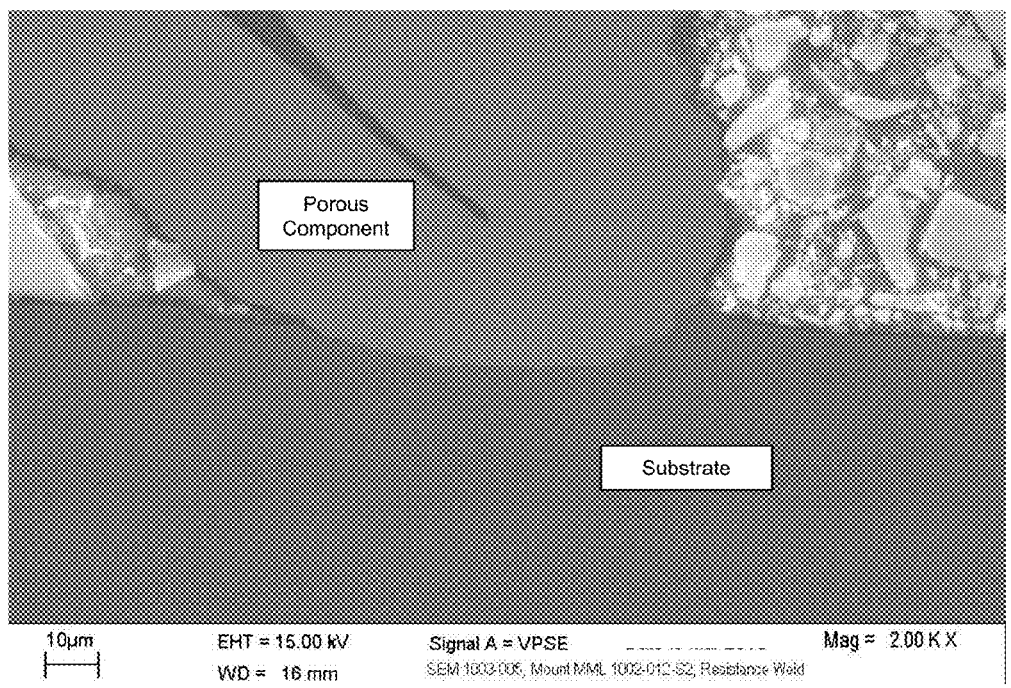
FIG. 11 is a scanning electron microscope image taken along the interface between a porous component and a substrate of a resistance welded sample.

When a porous component is resistance welded to an underlying substrate, little or no inter-diffusion occurs. For example, the tantalum concentration in the porous component remains substantially constant in FIG. 8, and the titanium concentration in the substrate remains substantially constant in FIG. 9. The lack of any significant inter-diffusion layer between the porous component and the substrate is also shown visually in FIG. 11, which is a scanning electron microscope image taken along the interface between the porous component and the substrate of a resistance welded sample.

5. Example #5

Analysis of Weld Pressure

A series of 1 inch (2.5 cm) diameter, disc-shaped samples were prepared, the electrode interface of each sample having a surface area of about 0.79 square inches (5.1 cm²). Each sample had a 0.055 inch (1.4 mm) thick porous component produced using Trabecular Metal™ technology and a 0.130 inch (3.3 mm) thick Tivanium® substrate. The weld pressure was calculated to be 4,160 psi (28.7 MPa), which was comparable to the compressive yield strength of the porous components. As a result of this high weld pressure, the porous components were partially crushed during welding and decreased in average thickness by about 0.022 inch (0.6 mm) or 40% (from 0.055 inch (1.4 mm) to 0.033 inch (0.8 mm)).

6. Example #6

Analysis of Pulse Welding

Another series of 1 inch (2.5 cm) diameter, disc-shaped samples were prepared, each sample having a 0.055 inch (1.4 mm) thick porous component produced using Trabecular Metal™ technology and a 0.130 inch (3.3 mm) thick Tivanium® substrate. Each porous component included an EDM-shaped surface interfacing with the substrate. The resistance welding parameters of Example #6 are set forth in Table 4 below.

TABLE 4

| Weld Parameter | Setting |
| --- | --- |
| Approach Pressure | 20 psi |
| Approach Time | 3 seconds |
| Weld Pressure | 800 psi |
| Forge Pressure | 45 psi |
| Forge Time | 3 seconds |
| Current | 24 kA |
| Current Density | 30 kA/in$^2$ |
| Controlled Atmosphere | argon |
|  | dew point < −60° C. |
|  | oxygen concentration < 10 ppm |

As set forth in Table 5 below, each sample received a different number of weld current pulses, with each pulse lasting 80 milliseconds and the cooling time between each pulse lasting 80 milliseconds. Samples 1-5 were prepared to evaluate up to 10 pulses. Samples 6-11 were prepared to more specifically evaluate between 5 and 10 pulses.

TABLE 5

| Sample | Number of Pulses |
| --- | --- |
| 1 | 1 |
| 2 | 4 |
| 3 | 6 |
| 4 | 8 |
| 5 | 10 |
| 6 | 5 |
| 7 | 6 |
| 8 | 7 |
| 9 | 8 |
| 10 | 9 |
| 11 | 10 |

A new resistance welding apparatus was designed and built to deliver these weld current pulses in a controlled environment. The apparatus included the AX5000 Atmospheric Enclosure with the BMI-500 Single-Column Gas Purification System, the KN-II Projection Weld Head with cooled, copper alloy electrodes, the IT-1400-3 Transformer, and the ISA-2000CR Inverter Power Supply, all of which are available from Miyachi Unitek Corporation of Monrovia, Calif.

The overall thickness of each sample remained substantially the same before and after welding, indicating that the lower 800 psi (5.5 MPa) weld pressure of Example #5 successfully eliminated the distortion and crushing of the porous component seen in Example #4 above.

Samples 1-5 were subjected to tensile testing. The tensile strength of the weld increased from 0 psi (0 MPa) for Sample 1 (1 pulse) to 6,882 psi (47.4 MPa) for Sample 3 (6 pulses). The tensile strength of the weld remained approximately the same for Sample 4 (8 pulses) and Sample 5 (10 pulses).

Figure 12:
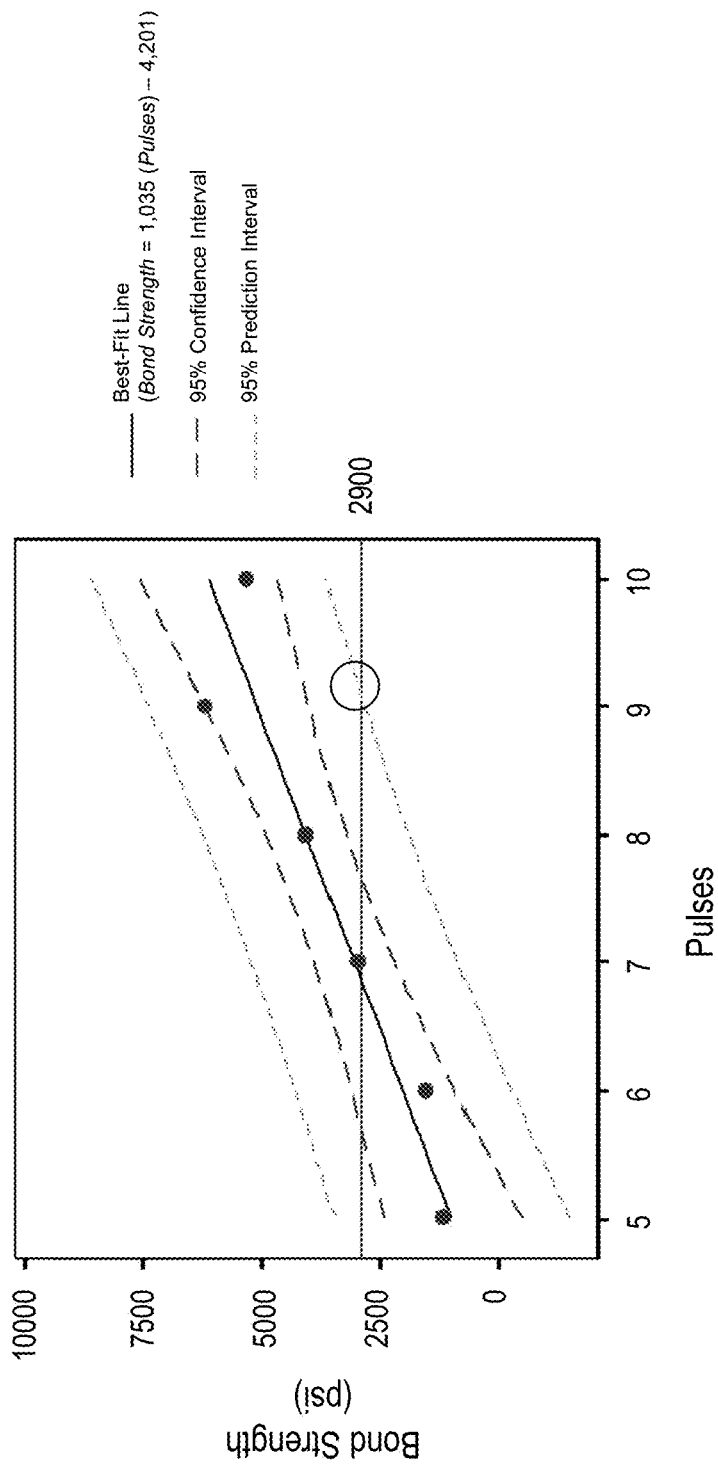
FIG. 12 is another graphical depiction of the bond strength between various porous layers and metal substrates in accordance with Example #6.

Samples 6-11 were then subjected to tensile testing and regression analysis, the results of which are presented graphically in FIG. 12. As shown in FIG. 12, the bond strength increased with each additional pulse. The lower 95% prediction interval intersects the 2,900 psi (20.0 MPa) reference line above 9 weld pulses (see circled intersection point in FIG. 12). Thus, at the given weld parameters, at least 10 weld pulses would be required to consistently produce bond strengths of at least 2,900 psi.

Visual inspection of the samples revealed the formation of noticeable heat-affected zones along both the bond interface (i.e., the interface between the porous component and the substrate) and the electrode interface (i.e., the interface between the sample and the resistance welding electrode).

Figure 13:
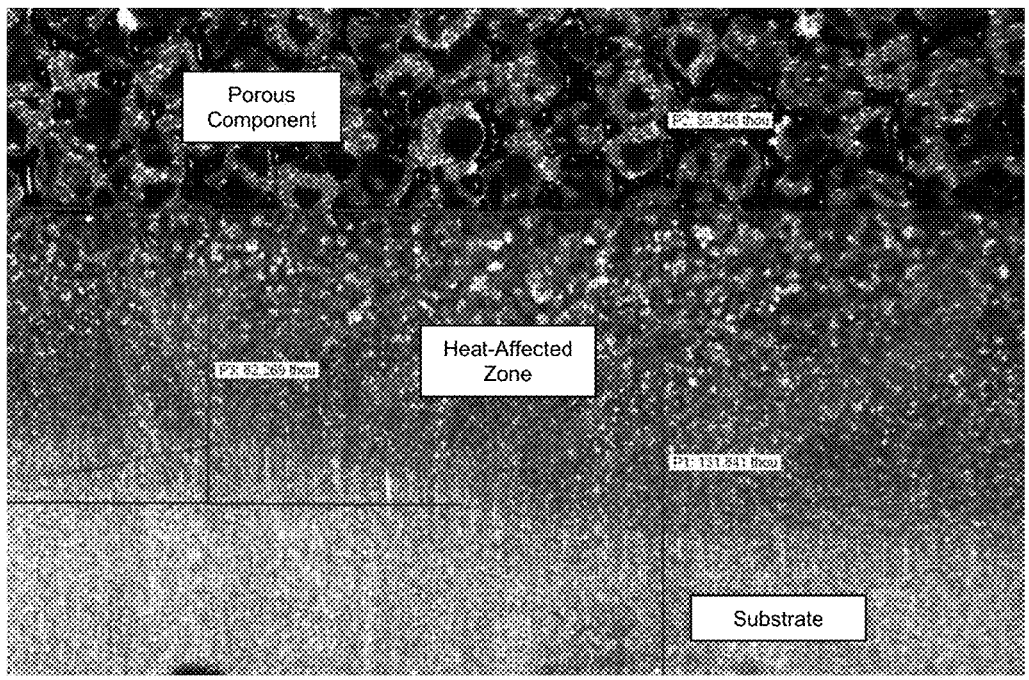
FIG. 13 is a scanning electron microscope image taken along the interface between a porous layer and metal substrate in accordance with Example #6.

Due to the heat generated during the resistance welding process, the samples may experience discoloration, bleed-through, and/or microstructure changes in such heat-affected zones. FIG. 13, for example, depicts the heat-affected zone that formed along the bond interface of Sample 1 above. It would be possible and within the scope of the present disclosure to machine away or otherwise remove the electrode interface after the resistance welding process. However, it would not be possible to remove the bond interface after the resistance welding process without destroying the bond.

7. Example #7

Analysis of Pulsed Weld Current to Reduce Heat-Affected Zones for Net-Shaped Porous Components To eliminate the heat-affected zones seen in Example #6 above, another series of 1 inch (2.5 cm) diameter, disc-shaped samples were prepared, each sample having a 0.055 inch (1.4 mm) thick porous component produced using Trabecular Metal™ technology and a 0.130 inch (3.3 mm) thick Tivanium® substrate. Unlike Example #6, each porous component included a net-shaped, not EDM-shaped, interfacing with the substrate. Also, compared to Example #6, the samples were subjected to shorter weld pulses, longer cooling times between pulses, higher weld pressures, and higher weld currents during resistance welding. The resistance welding parameters of Example #7 are set forth in Table 6 below.

TABLE 6

| Weld Parameter | Setting |
| --- | --- |
| Approach Pressure | 20 psi |
| Approach Time | 3 seconds |
| Weld Pressure | 1,000 psi |
| Forge Pressure | 62 psi |
| Forge Time | 3 seconds |
| Number of Pulses | 10 |
| Weld Time per Pulse | 15 milliseconds |
| Cooling Time | 250 milliseconds |
| Controlled Atmosphere | argon |
|  | dew point < −60° C. |
|  | oxygen concentration < 10 ppm |

As set forth in Table 7 below, the samples received pulsed weld currents between 35 kA and 51 kA.

TABLE 7

| | Weld Current Setting | Actual Weld Current (kA) | |
| --- | --- | --- | --- |
| Sample | (kA) | (for Pulse 1) | (for Pulses 2-10) |
| 1a | 35 | 33.9 | 34.3 |
| 1b | 35 | 33.9 | 34.3 |
| 2a | 39 | 37.5 | 38.0 |
| 2b | 39 | 37.6 | 38.0 |
| 3a | 43 | 41.0 | 41.7 |
| 3b | 43 | 41.2 | 41.6 |
| 4a | 47 | 43.7 | 45.1 |
| 4b | 47 | 44.3 | 45.2 |
| 5a | 51 | 46.9 | 48.5 |
| 5b | 51 | 46.9 | 48.5 |

Figure 14:
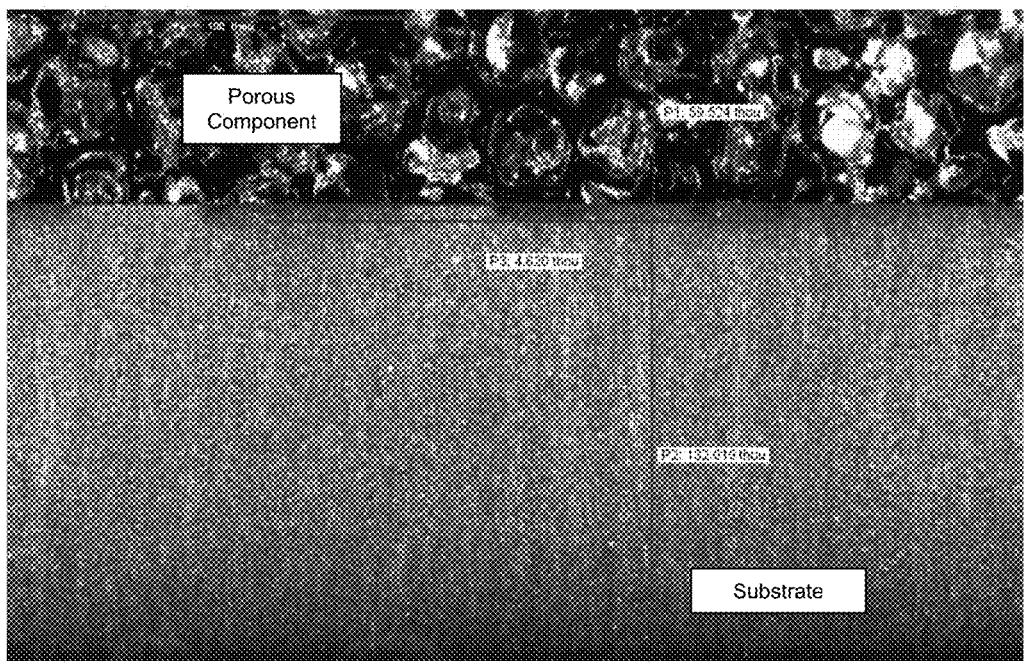
FIG. 14 is a scanning electron microscope image taken along the interface between a porous layer and metal substrate in accordance with Example #7.

As an initial matter, visual inspection of the samples showed that the depth and extent of the heat-affected zones along the bond interfaces were significantly reduced compared to Example #6 or, in some cases, were eliminated altogether. For example, Sample 1 of Example #6 (FIG. 13) has a noticeably larger heat-affected zone than Sample 3b of Example #7 (FIG. 14). Some heat-affected zones remained along the electrode interfaces, but as discussed above, it would be possible to machine away or otherwise remove these electrode interfaces after the resistance welding process.

Figure 15:
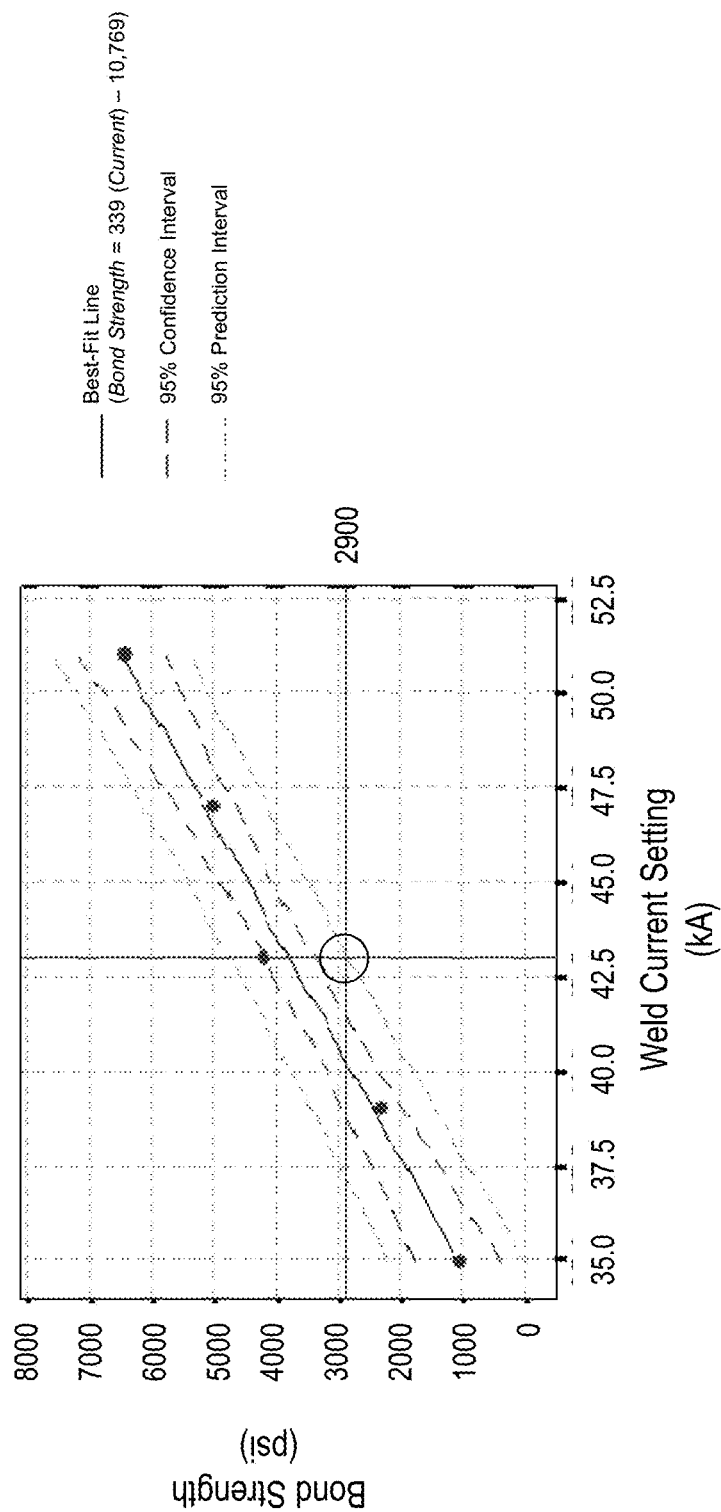
FIG. 15 is another graphical depiction of the bond strength between various porous layers and metal substrates in accordance with Example #7.

The samples were also subjected to tensile testing and regression analysis, the results of which are presented graphically in FIG. 15. As shown in FIG. 15, the bond strength increased as the weld current per pulse increased. The lower 95% prediction interval intersects the 2,900 psi (20.0 MPa) reference line at about 43 kA per pulse (see circled intersection point in FIG. 13). Thus, at the given weld parameters, a weld current of at least 43 kA per pulse (or a weld density of at least 54 kA/in$^2$ (8.4 kA/cm$^2$) per pulse) would be required to consistently produce bond strengths of at least 2,900 psi.

Additional samples were welded at 46 kA per pulse (or a weld density of about 58 kA/in$^2$ (9.0 kA/cm$^2$) per pulse) to confirm this result, but the bond strengths were inconsistent and ranged from 2,387 psi (16.5 MPa) to 4,246 psi (29.3 MPa). Also, visual inspection of these additional samples revealed noticeable heat-affected zones along the bond interfaces. The inventors attribute these inconsistent results, at least partially, to electrode wear and metal transfer onto the electrode.

8. Example #8

Analysis of Pulsed Weld Current to Reduce Heat-Affected Zones for EDM-Shaped Porous Components Example #7 was repeated with porous components having EDM-shaped (not net-shaped) surfaces interfacing with the substrate. None of the samples reached a bond strength of 2,900 psi (20.0 MPa). Also, the samples formed noticeable heat-affected zones along the bond interfaces.

9. Example #9

Analysis of Weld Pressure and Pulsed Weld Current to Reduce Electrode Damage and Improve Bond Strength To improve the results of Example #7, including reducing general electrode wear and metal transfer onto the electrode, Example #7 was repeated at a higher approach pressure of 40 psi (0.3 MPa), a higher weld pressure of 2,000 psi (13.8 MPa), and a lower forge pressure of 55 psi (0.4 MPa). In accordance with Example #7, the samples were subjected to pulsed weld currents greater than 43 kA, specifically between 45 kA and 61 kA.

At the higher weld pressure of Example #9 (2,000 psi), the inventors noticed less sticking between the samples and the electrodes than at the lower weld pressure of Example #7 (1,000 psi). The present inventors believe that the higher weld pressures increased contact between the samples and the electrodes, and therefore reduced the resistance and the heat generated between the samples and the electrodes.

The samples were subjected to tensile testing and regression analysis, which indicated that a weld current of at least 59 kA per pulse (or a weld density of at least 75 kA/in$^2$ (11.6 kA/cm$^2$) per pulse) would be required to consistently produce bond strengths of at least 2,900 psi (20.0 MPa).

Nine additional samples were welded at about 59 kA per pulse to confirm this result, and the bond strengths of these nine additional samples averaged 4,932 psi (34.0 MPa), ranging from 3,174 psi (21.9 MPa) to 6,688 psi (46.1 MPa). Also, visual inspection of these nine additional samples showed minimal presence of heat-affected zones along the bond interfaces.

Six additional samples were welded at about 61 kA per pulse (or a weld density of about 77 kA/in$^2$ (11.9 kA/cm$^2$) per pulse) to further confirm this result. Each of these additional samples had a slighter thicker substrate, specifically a 0.170 inch (4.3 mm) thick substrate, compared to previous tests, where the substrates were 0.130 inch thick (3.3 mm). The bond strengths of these additional samples averaged 3,968 psi (27.4 MPa), ranging from 3,259 psi (22.5 MPa) to 4,503 psi (31.0 MPa). In all of these additional samples, tensile failure occurred within the porous material, not along the bond interface between the porous material and the substrate. Also, visual inspection of these samples showed no macroscopic heat-affected zones along the bond interfaces. Furthermore, visual inspection of these samples showed microstructure changes along the electrode interfaces, but at very shallow, removable depths (e.g., less than 0.020 inch (0.5 mm) in depth).

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of manufacturing an orthopedic prosthesis comprising the steps of:
   providing a metal substrate;
   providing a previously-manufactured porous metal layer having a manufactured thickness, the previously-manufactured porous metal layer having a porosity of 55% to 90%;
   positioning the previously-manufactured porous metal layer against the metal substrate to form an interface between the previously-manufactured porous metal layer and the metal substrate, wherein said positioning generates a net contact area of 15% to 25% between the previously-manufactured porous metal layer and the metal substrate at said interface;
   applying a weld pressure holding the previously-manufactured porous metal layer against the metal substrate, wherein said weld pressure is at least 100 psi (0.7 MPa) but less than 3,000 psi (20.7 MPa), and wherein said net contact area is maintained despite applying said weld pressure; and
   directing an electrical current to the interface between the previously-manufactured porous metal layer and the metal substrate to resistance weld the previously-manufactured porous metal layer to the metal substrate while maintaining the manufactured thickness of the previously-manufactured porous metal layer.

2. The method of claim 1, wherein the previously-manufactured porous metal layer comprises a porous structure that includes an outer surface coated with metal.

3. The method of claim 1, wherein the previously-manufactured porous metal layer comprises a porous structure in the form of a layer that has an outer surface coated with a metal coating contacting the metal substrate at said interface.

4. The method of claim 1, wherein the previously-manufactured porous metal layer includes a plurality of ligaments defining open spaces therebetween, each of said ligaments including a carbon-containing core coated with metal contacting the metal substrate at said interface.

5. The method of claim 3, wherein said metal coating is chemical vapor deposited onto said outer surface and infiltrates said porous structure.

6. A method of manufacturing an orthopedic prosthesis having a metal substrate and a previously-manufactured porous metal layer, the method comprising the steps of:
   positioning the previously-manufactured porous metal layer against the metal substrate to form an interface between the previously-manufactured porous metal layer and the metal substrate;
   holding the previously-manufactured porous metal layer against the metal substrate with a weld pressure of at least 100 psi (0.7 MPa) but not exceeding a compressive yield strength of the previously-manufactured porous metal layer; and
   directing a pulsed electrical current to the interface between the previously-manufactured porous metal layer and the metal substrate to resistance weld the previously-manufactured porous metal layer to the metal substrate, the pulsed electrical current including at least a first pulse and a second pulse separated from the first pulse by a cooling time,
   wherein said positioning step generates a net contact area of 15% to 25% between the previously-manufactured porous metal layer and the metal substrate at said interface, and wherein said net contact area is maintained during said holding and directing steps.

7. The method of claim 6, wherein the weld pressure is less than 3,000 psi (20.7 MPa), and wherein the previously-manufactured porous metal layer includes a plurality of ligaments defining open spaces therebetween, each of said ligaments including a carbon-containing core coated with metal contacting the metal substrate at said interface.

8. The method of claim 6, wherein the directing step comprises directing each pulse of the pulsed electrical current to the orthopedic prosthesis at a current density of at least 75 kA/in$^2$ (11.6 kA/cm$^2$).

9. The method of claim 6, wherein the cooling time comprises less than 1 second.

10. The method of claim 6, wherein said previously-manufactured porous metal layer comprises a porous structure that includes an outer surface coated with a metal coating that is chemical vapor deposited onto said outer surface and infiltrates said porous structure.

11. The method of claim 6, wherein the previously-manufactured porous metal layer comprises a porous structure in the form of layer that has an outer surface coated with a metal coating contacting the metal substrate at said interface.

12. The method of claim 6, further comprising the steps of:
    applying a forge pressure to the orthopedic prosthesis after the directing step, wherein the forge pressure is less than the weld pressure.

13. The method of claim 6, wherein said previously-manufactured porous metal layer has a manufactured thickness prior to said positioning step, and wherein said manufactured thickness is maintained during said positioning and holding steps despite said weld pressure being at least 100 psi (0.7 MPa).

14. A method of manufacturing an orthopedic prosthesis comprising the steps of:
    providing a metal substrate;
    providing a previously-manufactured porous metal layer having a net surface, the net surface of the previously-manufactured porous metal layer being formed by:
       providing a porous structure having an outer surface;
       coating the outer surface of the porous structure with metal to produce the porous metal layer; and
       after the coating step, maintaining the outer surface without machining the outer surface to arrive at the net surface;
    positioning the net surface of the previously-manufactured porous metal layer against the metal substrate to form an interface between the previously-manufactured porous metal layer and the metal substrate, wherein said positioning generates a net contact area of 15% to 25% between the previously-manufactured porous metal layer and the metal substrate at said interface;
    holding the previously-manufactured porous metal layer against the metal substrate with a weld pressure of at least 100 psi but not exceeding a compressive yield strength of the previously-manufactured porous metal layer; and
    directing an electrical current to the interface between the porous metal layer and the metal substrate to resistance weld the previously-manufactured porous metal layer to the metal substrate, wherein said net contact area is maintained during the directing step.

15. The method of claim 14, wherein said positioning step avoids compressing the previously-manufactured porous metal layer.

16. The method of claim 14, wherein the previously-manufactured porous metal layer has a porosity of 55% to 90%.

17. The method of claim 14, wherein the porous structure comprises reticulated vitreous carbon foam.

18. The method of claim 14, wherein the coating step comprises a chemical vapor deposition step to coat the outer surface of the porous structure with metal and to infiltrate the porous structure with metal.

19. The method of claim 14, wherein said weld pressure is less than 3,000 psi.

20. A method of manufacturing an orthopedic prosthesis comprising the steps of:
    providing a metal substrate;
    providing a previously-manufactured porous metal layer having a manufactured thickness, wherein the previously-manufactured porous metal layer includes a porous structure in the form of a layer that has an outer surface coated with a metal coating forming an outer coated surface;
    positioning the previously-manufactured porous metal layer against the metal substrate so that said outer coated surface contacts the metal substrate at an interface, wherein said positioning generates a net contact area of 15% to 25% between the previously-manufactured porous metal layer and the metal substrate at said interface, and wherein said positioning step maintains said manufactured thickness yet includes applying a weld pressure of at least 100psi (0.7 MPa) holding the previously-manufactured porous metal layer against the metal substrate; and
    directing an electrical current to the interface to resistance weld the previously-manufactured porous metal layer to the metal substrate.

21. The method of claim 20, wherein said metal coating is chemical vapor deposited onto said outer surface.

* * * * *